(12) United States Patent
Baker, III et al.

(10) Patent No.: US 7,729,767 B2
(45) Date of Patent: Jun. 1, 2010

(54) IMPLANTABLE GENERATING SYSTEM

(76) Inventors: Rex M. Baker, III, 3 School St., Harrisville, NH (US) 03450; James R. Baker, P.O. Box 6, Zionsville, PA (US) 18092

( * ) Notice: Subject to any disclaimer, the term of this patent is extended or adjusted under 35 U.S.C. 154(b) by 617 days.

(21) Appl. No.: 11/058,403

(22) Filed: Feb. 15, 2005

(65) Prior Publication Data

US 2006/0184206 A1 Aug. 17, 2006

(51) Int. Cl.
*A61N 1/378* (2006.01)
(52) U.S. Cl. .................................................. 607/35
(58) Field of Classification Search ................ 607/35; 310/311, 340; 322/1; 623/3.12
See application file for complete search history.

(56) References Cited

U.S. PATENT DOCUMENTS

| | | | |
|---|---|---|---|
| 2,029,148 A | 1/1936 | Archer | |
| 3,693,625 A * | 9/1972 | Auphan | 607/19 |
| 4,245,640 A | 1/1981 | Hunt | |
| 4,788,669 A * | 11/1988 | Kamiyama | 368/80 |
| 5,431,694 A * | 7/1995 | Snaper et al. | 607/35 |
| 5,540,729 A * | 7/1996 | Weijand | 607/35 |
| 5,923,619 A | 7/1999 | Knapen et al. | |
| 6,822,343 B2 * | 11/2004 | Estevez | 290/1 R |
| 7,081,683 B2 * | 7/2006 | Ariav | 290/1 R |
| 2004/0073267 A1 | 4/2004 | Holzer | |

OTHER PUBLICATIONS

International Search Report with Written Opinion dated Aug. 7, 2007 received in International Patent Application No. PCT/US06/04272 (9 pages).

* cited by examiner

*Primary Examiner*—Carl H. Layno
*Assistant Examiner*—Tammie K Heller
(74) *Attorney, Agent, or Firm*—Holland & Knight LLP; Brian J. Colandreo, Esq.; J. Mitchell Herbert, Jr., Esq.

(57) ABSTRACT

An implantable generating system includes a generator assembly configured to be positioned within a living organism for converting mechanical motion into electrical energy. A linkage assembly is configured to be positioned within the living organism for mechanically coupling the generator assembly with one or more body parts displaceable during respiratory-based diaphragm motion.

15 Claims, 7 Drawing Sheets

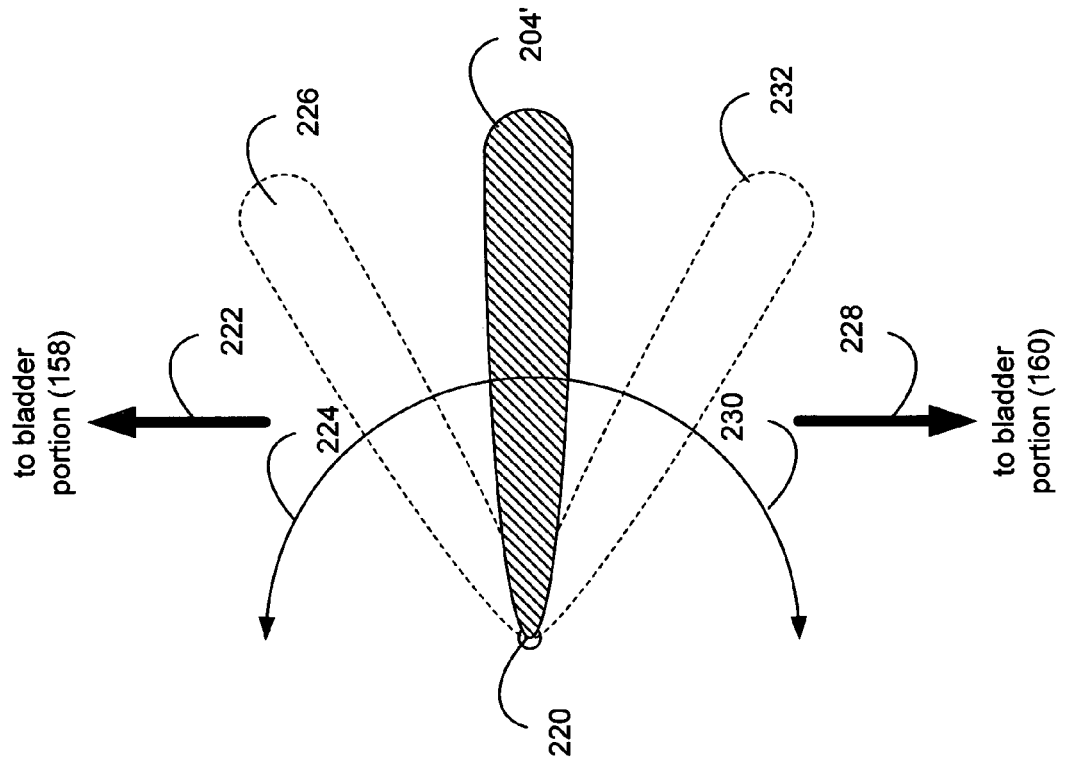
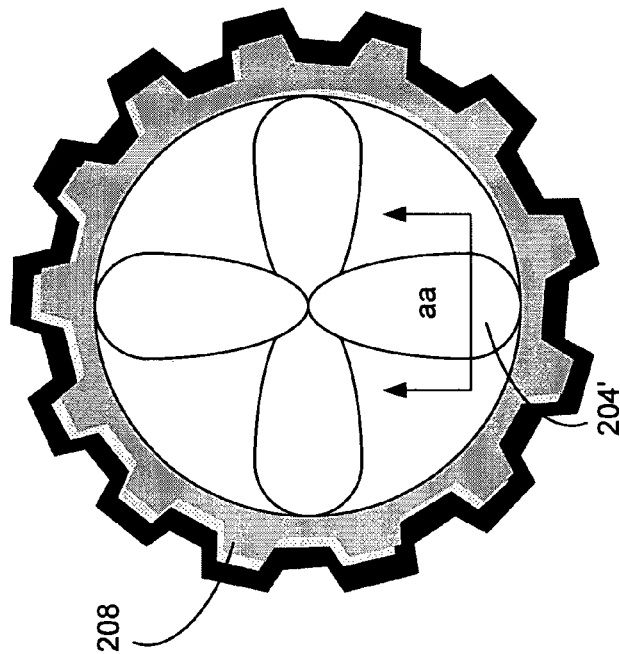
Fig. 4a
Fig. 4b

IMPLANTABLE GENERATING SYSTEM

FIELD OF THE DISCLOSURE

This disclosure relates to electrical generation systems and, more particularly, to implantable electrical generation systems.

BACKGROUND

Medical devices are often implanted into humans and animals as a means for achieving a desired result. Examples of these implanted medical devices include: pacemakers (i.e., a device used to stimulate or regulate contractions of the heart muscle); defibrillators (i.e., a device used to counteract fibrillation of the heart muscle and restore a normal heartbeat by applying a brief electric shock); bone growth stimulation devices, pain blocking/attenuation devices, brain implant devices, and cochlear implant devices, for example. Typically, these devices are powered by an internal battery or external battery pack (i.e., a battery pack implanted within the patient but external to the medical device).

Unfortunately, these batteries/battery packs have a finite life span and, after a period of time, must be replaced. Regardless of the type of battery/battery pack used by the medical device, surgery is required and, for those devices that use internal batteries, device removal/replacement is also required.

SUMMARY OF THE DISCLOSURE

According to an aspect of this invention, an implantable generating system includes: a generator assembly for converting mechanical motion into electrical energy. A linkage assembly, which is mechanically coupled to the generator assembly, converts respiratory motion into mechanical motion.

One or more of the following features may also be included. An energy storage device (e.g., a battery or a capacitor) may be electrically coupled to the generator assembly to store the electrical energy. The generator assembly may include a rotor assembly and a stator assembly. A freewheel clutch assembly, positioned between the rotor assembly and the linkage assembly, may allow for mono-directional rotation of the rotor assembly independent of the linkage assembly. A flywheel assembly may store the rotational kinetic energy of the rotor assembly.

The linkage assembly, which is configured to convert respiratory motion into rotational motion of the rotor assembly, may include at least one rack gear assembly mechanically coupled on a first end to a portion of a rib cage, such that the portion of the rib cage moves in response to respiratory motion. A pinion gear assembly may be mechanically coupled to the rotor assembly, and a second end of the at least one rack gear assembly may be configured to mesh with the pinion gear assembly, such that linear movement of the rack gear assembly is converted to rotational movement of the pinion gear assembly and the rotor assembly.

The linkage assembly, which is configured to convert respiratory motion into rotational motion of the rotor assembly, may include a fluid-filled bladder assembly that penetrates an abdominal diaphragm, such that a first portion of the bladder assembly is positioned on a first side of the abdominal diaphragm and a second portion of the bladder assembly is positioned on a second side of the abdominal diaphragm. An impeller assembly may be positioned between the first and second portions of the bladder assembly. The impeller assembly may be mechanically coupled to the rotor assembly of the generator assembly. As the abdominal diaphragm systematically moves in response to respiratory motion, the fluid within the bladder assembly may be repeatedly displaced from one of the portions of the bladder assembly to the other portion of the bladder assembly, passing through and rotating the impeller assembly.

The generator assembly may include a coil assembly and magnetic core assembly axially displaceable within the coil assembly. The linkage assembly may include at least one rod assembly mechanically coupled on a first end to an abdominal diaphragm, such that the abdominal diaphragm systematically moves in response to respiratory motion. A second end of the at least one rod assembly may be mechanically coupled to the magnetic core assembly and movement of the at least one rod assembly may result in axial displacement of the magnetic core assembly within the coil assembly. The at least one rod assembly may include a magnetic coupling assembly configured to temporarily uncouple the first and second ends of the rod assembly during irregular movement of the diaphragm.

According to another aspect of this invention, an implantable system includes a medical device. An energy storage device, which is electrically coupled to the medical device, provides electrical energy to the medical device. An implantable generating system, which is electrically coupled to the energy storage device, converts respiratory motion into electrical energy that is provided to the energy storage device.

One or more of the following features may also be included. The medical device may be a pacemaker, a defibrillator, a bone growth stimulation device, or a pain attenuation device, for example. The implantable generating system may include a generator assembly having a rotor assembly and a stator assembly, and a linkage assembly, mechanically coupled to the generator assembly, for converting respiratory motion into mechanical motion. The generator assembly may include a coil assembly and magnetic core assembly axially displaceable within the coil assembly.

According to another aspect of this invention, a method of providing electrical energy to an implanted medical device includes rigidly affixing an implantable generating system into a breathing organism, mechanically coupling the implantable generating system to a portion of the breathing organism that exhibits respiratory motion, and electrically coupling the implantable generating system to the implanted medical device.

One or more of the following features may also be included. The breathing organism may be a human being or an animal, for example. The medical device may be a pacemaker, a defibrillator, a bone growth stimulation device, or a pain attenuation device, for example. The portion of the breathing organism that exhibits respiratory motion may be a portion of a rib cage or an abdominal diaphragm, for example.

The details of one or more implementations are set forth in the accompanying drawings and the description below. Other features and advantages will become apparent from the description, the drawings, and the claims.

BRIEF DESCRIPTION OF THE DRAWINGS

FIG. 4a is a more detailed view of an alternative embodiment of the bladder-type implantable generation system of FIG. 3;

FIG. 4b is a cross-sectional view of the alternative embodiment of the bladder-type implantable generation system of FIG. 4a;

DETAILED DESCRIPTION OF THE PREFERRED EMBODIMENTS

Figure 1:
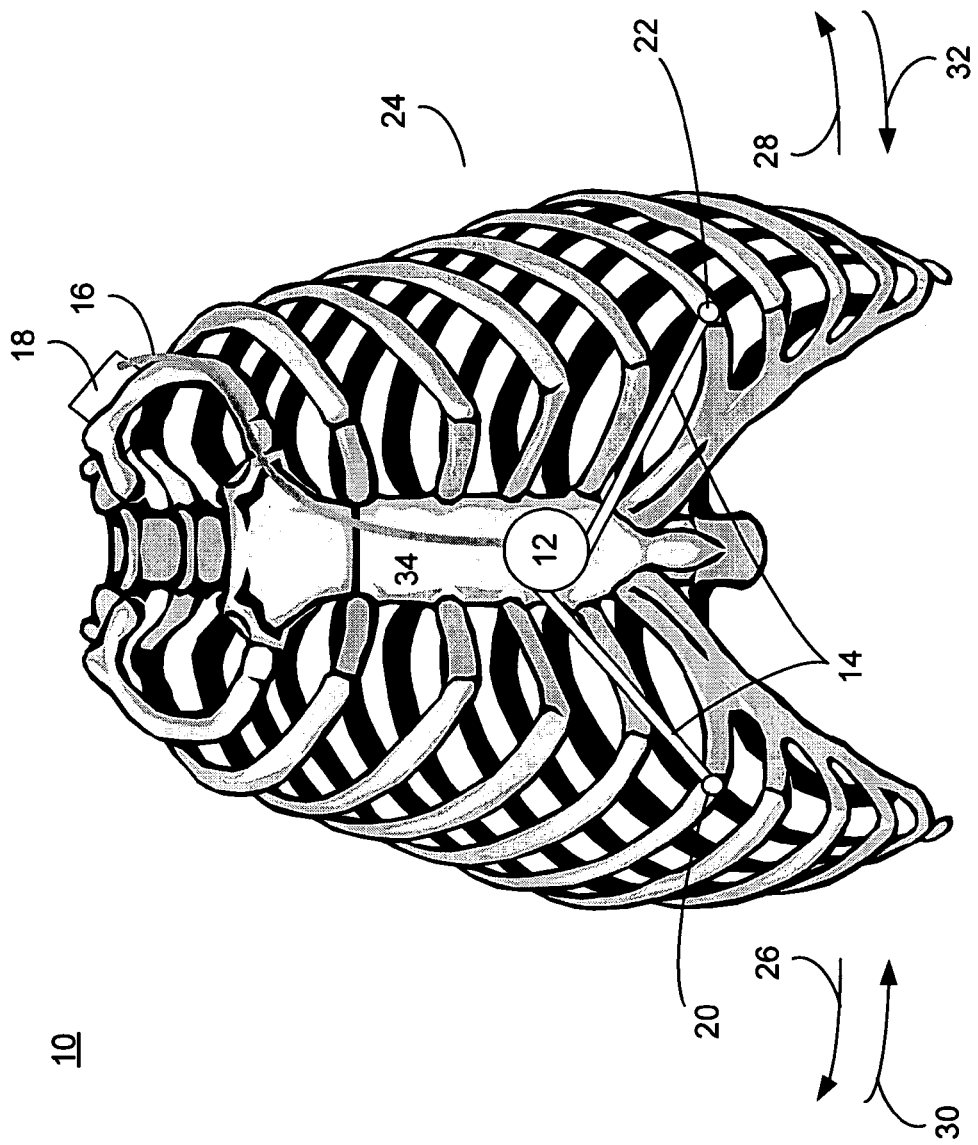
FIG. 1 is a diagrammatic view of an implantable generation system coupled to a rib cage.

Referring to FIG. 1, there is shown an implantable generation system 10 that includes a generator assembly 12 and a linkage assembly 14. Implantable generation system 10 may be implanted into any breathing organism (e.g., a human being or an animal) and is typically constructed of an implantable material (e.g., surgical steel, platinum, ceramic, cobalt chromium alloy, and/or ferric magnets). Generator assembly 12 is typically an alternating current or direct current generator (to be discussed below in greater detail) that generates electrical energy that is supplied (via lead 16) to implanted medical device 18. Examples of medical device 18 include a pacemaker, a defibrillator, a bone growth stimulation device, a pain attenuation device, a brain implant device, a cochlear implant device, a sphincter muscle stimulation device, for example.

In this embodiment, linkage assembly 14 mechanically couples generator assembly 12 to two portions 20, 22 of the rib cage 24 that move during respiration. Specifically, as a person breathes, their ribcage expands in the direction of arrows 26, 28 and when that person exhales, their rib cage contracts in the direction of arrows 30, 32. Linkage 14, which is typically pivotally connected to rib cage 24, captures this respiratory motion and uses it to e.g., turn generator assembly 12 (which is typically rigidly coupled to the sternum 34). Generator assembly 12 may be fastened to sternum 34 using any traditional surgical fasteners, such as surgical adhesives, staples, or screws, for example.

For illustrative purposes, generator assembly 12 and linkage assembly 14 are shown as being installed on the outside of the rib cage 24. However, generator assembly 12 and linkage assembly 14 are typically installed on the inside of rib cage 24.

Figure 2:
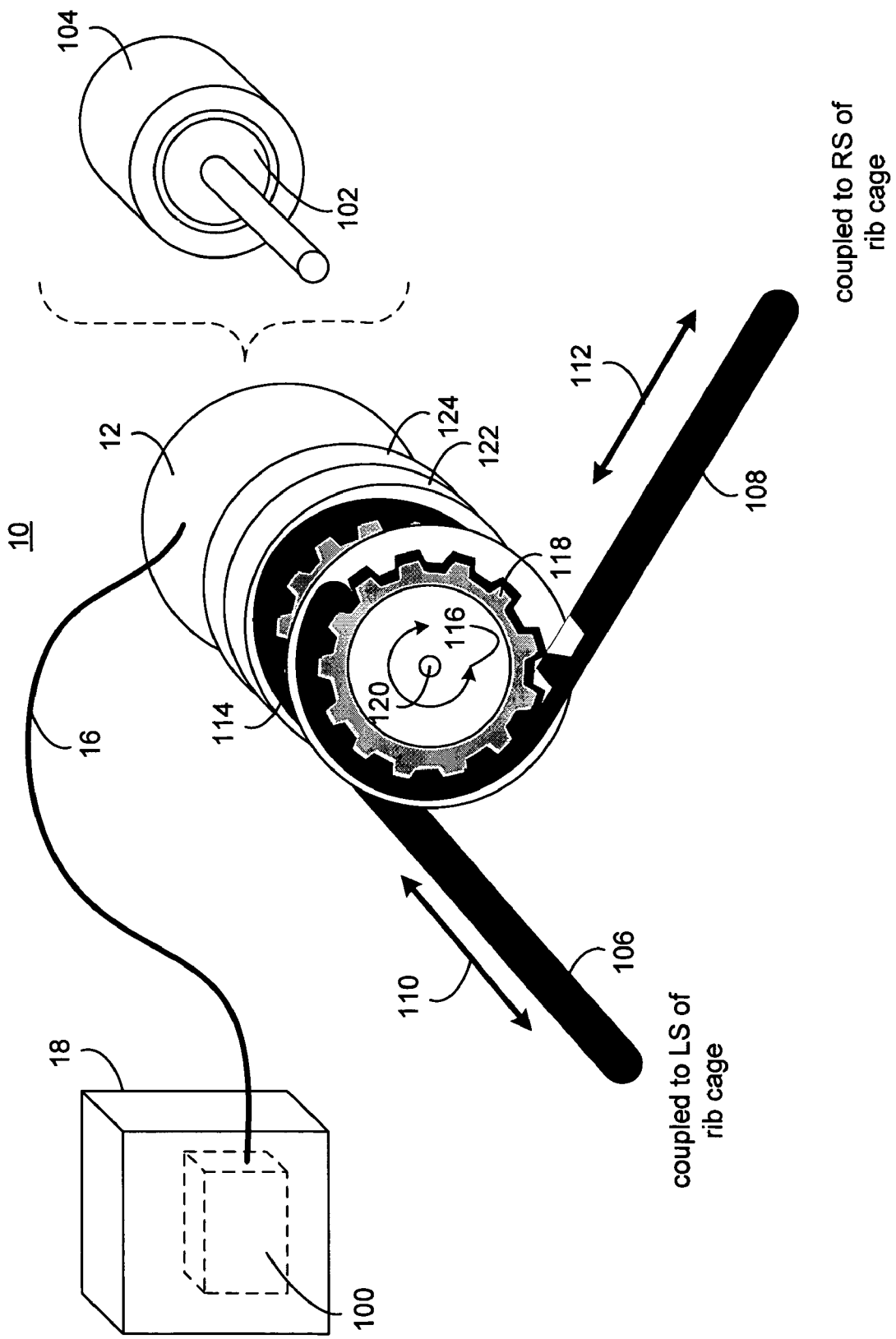
FIG. 2 is a more detailed view of the implantable generation system of FIG. 1.

Referring also to FIG. 2, there is shown a more detailed view of implantable generation system 10. As stated above, implantable generation system 10 is electrically coupled to medical device 18, which typically includes an energy storage device 100, such as a lithium ion battery. Implantable generation system 10 is typically configured to provide a low-rate charge to energy storage device 100, thus extending the useful life of energy storage device 100.

Further, a redundant battery (not shown) may be connected in series between implantable generation system 10 and energy storage device 100 of medical device 18. This redundant battery would, in turn, provide a level of redundancy in the event that implantable generation system 10 prematurely fails.

Typically, generator assembly 12 is a DC-type generator that includes a rotor assembly 102 and a stator assembly 104, such that stator assembly 104 is a compact design that utilizes permanent magnets (not shown) to generator a magnetic field. As is known in the art, when rotor assembly 102 is rotated through the magnetic field generated by the permanent magnets of stator assembly 104, a current signal is induced in the windings (not shown) of rotor assembly 102. Depending on whether or not the rotor assembly includes a commutator, the current signal generated may need to be rectified. Typically, the current signal is converted to a voltage signal through the charging and discharging of one or more capacitors.

As described above, during normal respiration, the rib cage expands and contracts, resulting in the movement of linkage assembly 14. In this embodiment, linkage assembly 14 includes two rack gear assemblies 106, 108, each of which moves in the direction of arrows 110, 112 (respectively). As rack gear assembly 106 moves in the direction of arrow 110, pinion gear assembly 114 rotates in a systematic clockwise/counterclockwise fashion (as indicated by arrow 116). Further, as rack gear assembly 108 moves in the direction of arrow 112, pinion gear assembly 118 rotates in a systematic clockwise/counterclockwise fashion (also as indicated by arrow 116). This repeated clockwise/counterclockwise rotation of pinion gear assemblies 114, 118 results in the clockwise/counterclockwise rotation of clutch drive shaft 120. Typically, rack gear assemblies 106, 108 are constructed of a material that is rigid enough to avoid deflection and buckling when compressed, yet flexible enough so that the material can bend (i.e., wrap) around the surface of the pinion gear assembly with which it is meshing. Examples of such a material include medical nylon, low friction polyethylene, and polypropylene.

Typically, a freewheel clutch assembly 122 is positioned between pinion gear assemblies 114, 118 and generator assembly 12. A freewheel clutch assembly is a power-transmission device that allows the drive shaft of a device (i.e., generator assembly 12) to continue turning in a first direction (e.g., clockwise) even when the shaft (i.e., clutch drive shaft 120) driving freewheel clutch assembly 122 is turning in an opposite direction (e.g., counterclockwise). Accordingly, freewheel clutch assembly 122 converts the bidirectional rotation of clutch drive shaft 120 into mono-directional rotation that turns rotor assembly 102. A typical example of freewheel clutch assembly 122 is the type of freewheel clutch assembly utilized in a self-winding wrist watch.

Additionally, a flywheel assembly 124 may be positioned between pinion gear assemblies 114, 118 and generator assembly 12. During operation, flywheel assembly 124 stores rotational kinetic energy so that rotor assembly 102 rotates smoothly and consistently even though the rotational energy is provided from freewheel clutch assembly 124 to rotor assembly 102 in a ratcheting fashion.

In addition, a step-up or step-down gear assembly (not shown) may be positioned between freewheel clutch assembly 122 and generator assembly 12 so that the rotational speed of generator assembly 12 may be increased or decreased with respect to the rotational speed of freewheel clutch assembly 122.

As an alternative to the embodiment described above, freewheel clutch assembly 122 may be configured such that both inhalation and exhalation result in rotation of generator assembly 12.

Figure 3:
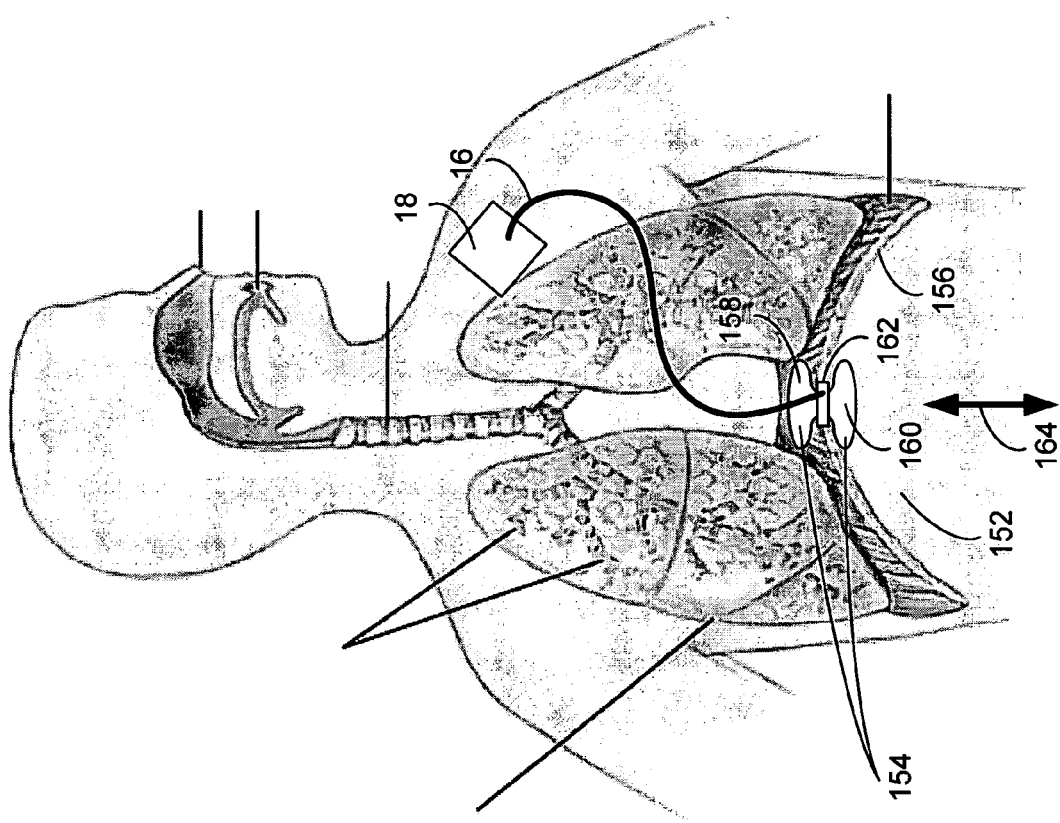
FIG. 3 is a diagrammatic view of a bladder-type implantable generation system.
Figure 4:
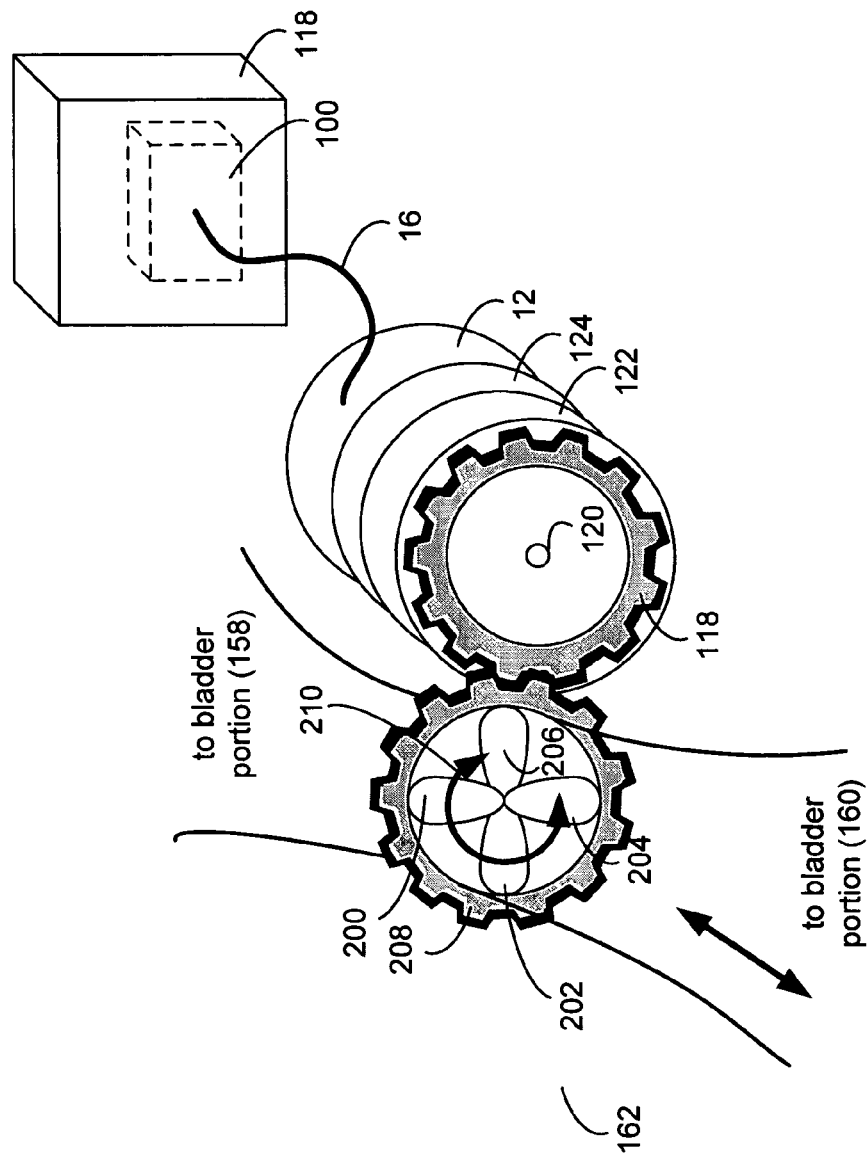
FIG. 4 is a more detailed view of the bladder-type implantable generation system of FIG. 3.

Referring to FIGS. 3 and 4, there is shown a bladder-type implantable generation system 150 in which the linkage assembly 152 includes a fluid-filled bladder assembly 154 that penetrates the abdominal diaphragm 156 of the patient. A first portion 158 of bladder assembly 154 is positioned on a first side of abdominal diaphragm 156, and a second portion 160 of bladder assembly 154 is positioned on a second side of abdominal diaphragm 156. Typical examples of the fluid within bladder assembly 154 include an inert gas, a saline solution, and water. An impeller assembly 162 is positioned between the first and second portions 158, 160 of the fluid-filled bladder assembly 154. Typically, impeller assembly 162 is positioned proximate the portion of the abdominal diaphragm 156 through which the fluid-filled bladder assembly 154 passes.

Referring also to FIG. 4, impeller assembly 162 includes one or more blade assemblies 200, 202, 204, 206 angled such that the passing of fluid from one of the bladder portions (e.g., portion 158) to the other bladder portion (e.g., portion 160) results in the rotation of impeller assembly 162. Impeller assembly 162 additionally includes an impeller gear assembly 208 that meshes with gear assembly 118.

Since, during normal respiratory motion, the abdominal diaphragm systematically moves in the direction of arrow 164, the fluid within fluid-filled bladder assembly 154 is repeatedly cycled between the first and second portions 158, 160 of the bladder assembly 154. Specifically, as the abdominal diaphragm move upward, the first portion 158 of fluid-filled bladder assembly 154 is compressed and fluid is evacuated from the first portion 158 to the second portion 160. Conversely, when the abdominal diaphragm moves downward, the second portion 160 of bladder assembly 154 is compressed and fluid is evacuated from the second portion 160 to the first portion 158. This repeated moving of the diaphragm results in the cycling of fluid from the first portion 158, to the second portion 160, to the first portion 158, and so on. This, in turn, results in impeller assembly 162 cyclically rotating in the direction of arrow 210, which in turn rotates gear assembly 118 and, therefore, generator assembly 12.

As discussed above, a freewheel clutch assembly 122 is typically employed to convert the bidirectional rotation of clutch drive shaft 120 into mono-directional rotation of the rotor assembly. Further, a flywheel assembly 124 is typically positioned between gear assembly 118 and generator assembly 12 to store rotational kinetic energy.

In addition to the embodiment shown in FIG. 4, other configurations are possible. For example, impeller assembly 162, freewheel clutch assembly 122, flywheel assembly 124, and generator assembly 12 may be coaxially aligned. Further, clutch drive shaft 120 may be sufficient long to allow for the positioning of impeller assembly 162 within bladder assembly 154, the penetration of shaft 120 through bladder assembly 154, and the positioning of freewheel clutch assembly 122, flywheel assembly 124, and generator assembly 12 outside of bladder assembly 154. Alternatively still, impeller assembly 162, freewheel clutch assembly 122, flywheel assembly 124, and generator assembly 12 may be a unitary structure positioned within bladder assembly 154, such that only lead 16 penetrates bladder assembly 154.

Referring to FIGS. 4a & 4b, while generator assembly 12 is described above as utilizing a freewheel clutch assembly, other configurations are possible. For example, blade assemblies 200, 202, 204, 206 may be variable-pitch blade assemblies configured such that a change in flow direction (i.e., into bladder portion 158 versus into bladder portion 160) reverses the pitch of the blade assemblies. A cross-sectional view (along section line a-a of FIG. 4a) of a variable-pitch blade assembly 204' is shown in FIG. 4b. Variable pitch blade assembly 204' is configured to pivot about pivot point 220, such that the direction of pivotal rotation is controlled by the direction of fluid flow. For example, when fluid is flowing in the direction of arrow 222 (i.e., toward upper bladder portion 158), variable pitch blade assembly 204" pivots about arc 224 toward blade position 226 (shown in phantom). Conversely, when fluid is flowing in the direction of arrow 228 (i.e., toward lower bladder portion 160), variable pitch blade assembly 204' pivots about arc 230 toward blade position 232 (also shown in phantom). Accordingly, by reversing the blade pitch in response to a reverse in the direction of fluid flow, generator assembly 12 is allowed to rotate in the same direction regardless of whether the person is inhaling or exhaling.

Figure 5:
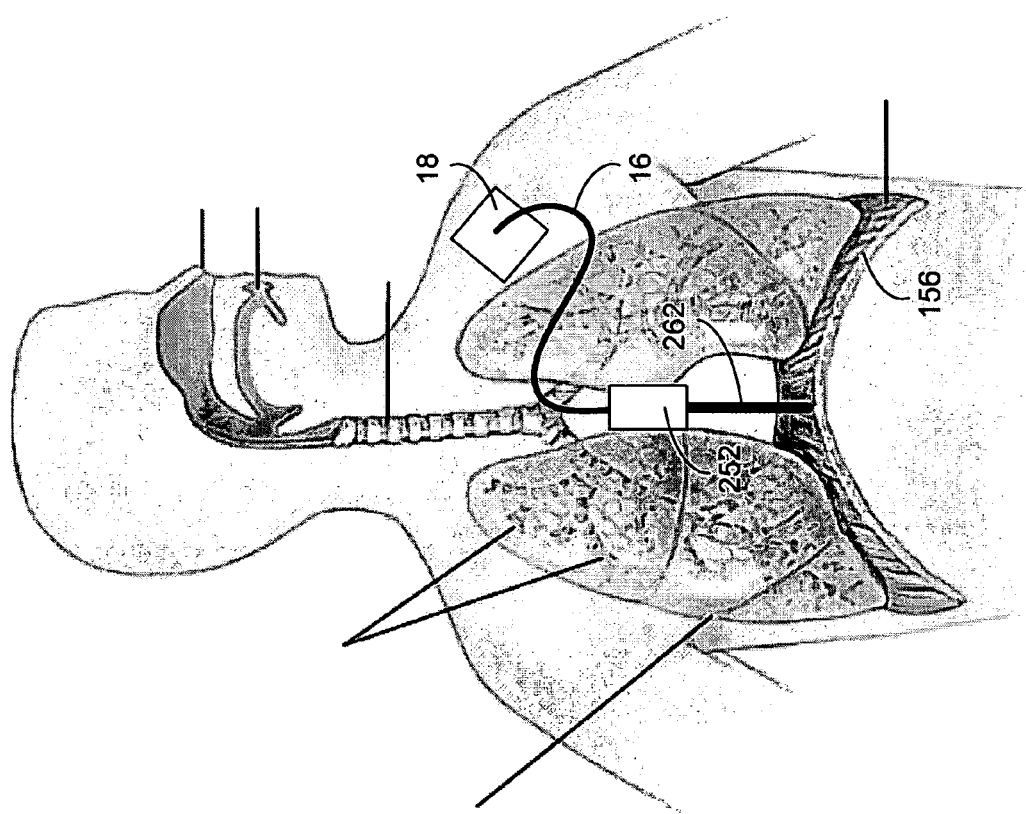
FIG. 5 is a diagrammatic view of an implantable generation system coupled to an abdominal diaphragm.
Figure 6:
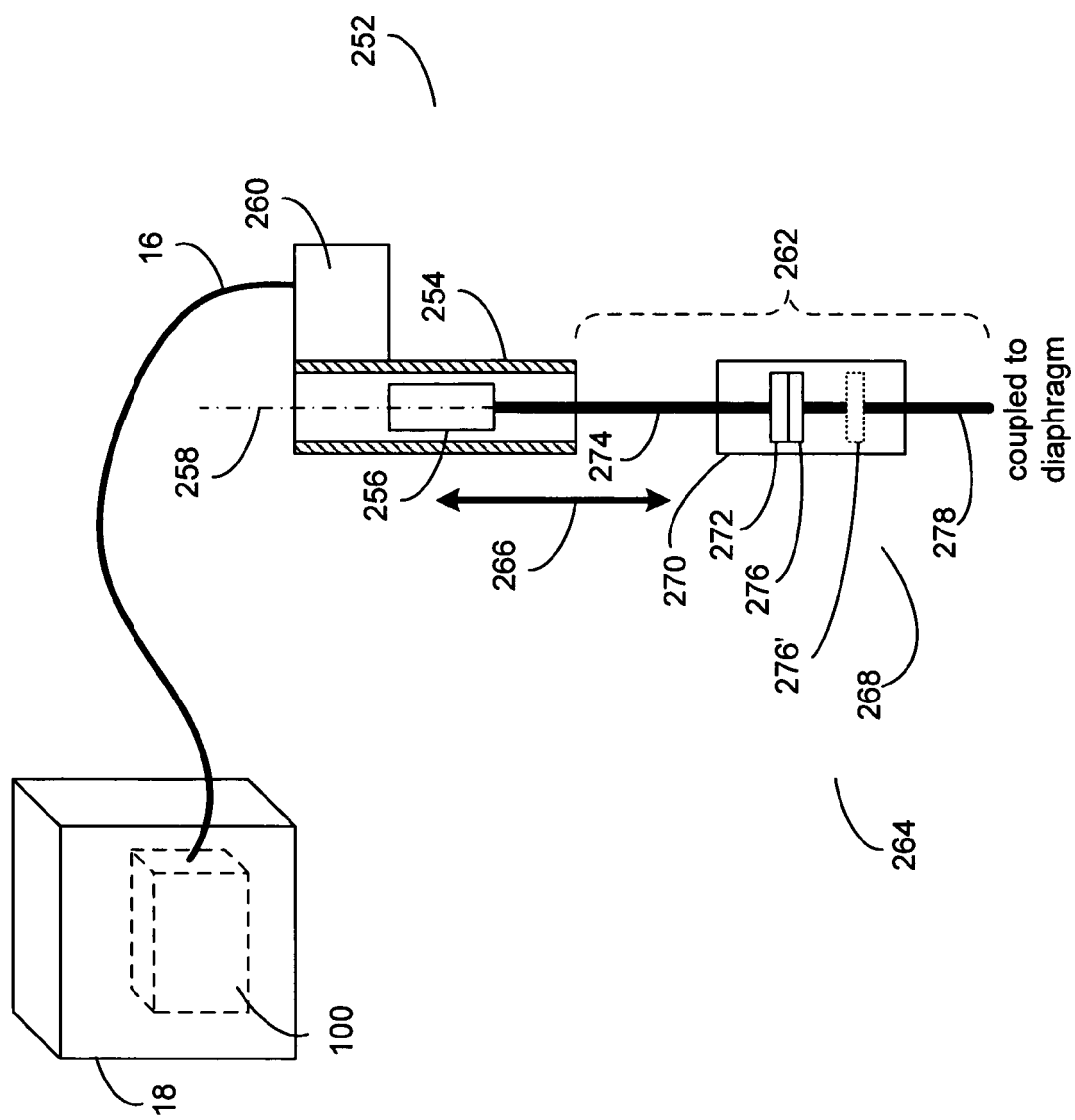
FIG. 6 is a more detailed view of the implantable generation system of FIG. 5.

Referring to FIGS. 5 & 6, there is shown an alternative embodiment of the implantable generation system 250 in which the generator assembly 252 includes a coil assembly 254 and a magnetic core assembly 256 linearly displaceable along the axis 258 of coil assembly 254. Coil assembly 252 is typically a helically wound conductor coil. As is known in the art, when magnetic core assembly 256 is linearly displaced within coil assembly 254, a current is induced within the conductor coil. As described above, this current signal is typically processed by processing circuitry 260 (e.g., rectifier circuitry and capacitive circuitry, for example) to produce a voltage signal that is supplied (via lead 16) to the energy storage device 100 within medical device 18.

As described above, abdominal diaphragm 156 repeatedly moves upward and downward during normal respiratory motion. Linkage assembly 262 includes a rod assembly 264 that is connected on a first end to abdominal diaphragm 156. Rod assembly 264 may be coupled to diaphragm 156 using any means known in the art, such as sutures or surgical staples, for example. As the abdominal diaphragm moves upward and downward during normal respiratory motion, rod assembly 264 also moves upward and downward in the direction of arrow 266. The second end of rod assembly 264 is coupled to the magnetic core 256 of generator assembly 252. Accordingly, during normal repository motion, magnetic core assembly 256 moves upward and downward within coil assembly 254, resulting in the generation of a voltage signal that is supplied to medical device 18.

Since abdominal diaphragm 156 may move violently (i.e., irregularly) during certain events (e.g., hiccupping or vomiting, for example), a magnetic coupling assembly 268 allows for the temporarily uncoupling of the first end of rod assembly 264 (i.e., the end coupled to abdominal diaphragm 156) from the second end of the rod assembly 264 (i.e., the end coupled to magnetic core assembly 256). One embodiment of magnetic coupling assembly 268 may include a sleeve assembly 270, a first magnet 272 connected to the upper portion 274 of rod assembly 264, and a second magnet 276 connected to the lower portion 278 of rod assembly 264. Magnets 272, 276 are configured so that they normally attract and contact each other. However, in the event that abdominal diaphragm 156 moves downward to an extent that exceeds the maximum distance that magnetic core assembly 256 can travel within coil assembly 254, the two magnets 272, 276 separate, allowing the lower portion 278 of rod assembly 264 to travel an enhanced distance (as shown by magnet 276'), reducing the possibility of injury to abdominal diaphragm 156.

Magnetic coupler assembly 268 may also be incorporated into the previously-described embodiments. For example, magnetic coupler assembly 268 may be incorporated into one or both rack gear assemblies 106, 108 (See FIG. 2), thus allowing for temporary uncoupling of the generator assembly from the rib cage in the event of violent movement of the rib cage.

While magnetic coupler assembly 268 is described above as allowing for temporary uncoupling in the event of violent downward movement of the diaphragm, other configurations are possible. For example, magnetic coupler assembly 268 may be configured such that any violent movement (i.e., upward or downward) results in the temporary uncoupling of magnetic coupler assembly 268.

While various type of implantable generation systems are described above, each of which uses a specific linkage assembly, other configurations are possible. For example, the embodiment described above that uses a rod assembly coupled to the abdominal diaphragm may be used with a generator assembly including a rotor and a stator assembly, provided the rod assembly is configured similarly to that of the rack gear assemblies described above. Further, the embodiment described above that uses rack gear assemblies coupled to a portion of the rib cage may be used with a generator assembly that includes a coil assembly and a magnetic core assembly, provided the rack gear assemblies are configured similarly to that of the rod assembly described above.

A number of implementations have been described. Nevertheless, it will be understood that various modifications may be made. Accordingly, other implementations are within the scope of the following claims.

What is claimed is:

1. An implantable generating system comprising:
    a generator assembly configured to be coupled to at least a portion of a rib cage of a living organism for converting mechanical motion into electrical energy, wherein the generator assembly includes a rotor assembly and a stator assembly;
    a linkage assembly configured to be positioned within the living organism for mechanically coupling the generator assembly with at least a portion of the rib cage displaceable during respiratory-based diaphragm motion; and
    a freewheel clutch assembly, positioned between the rotor assembly and the linkage assembly, for allowing mono-directional rotation of the rotor assembly independent of the linkage assembly.

2. The system of claim 1 further comprising an energy storage device electrically coupled to the generator assembly for storing the electrical energy.

3. The system of claim 2 wherein the energy storage device is one of a battery and a capacitor.

4. The system of claim 1 further comprising a flywheel assembly for storing the rotational kinetic energy of the rotor assembly.

5. The system of claim 1 wherein the linkage assembly, which is configured to convert respiratory-based diaphragm motion into rotational motion of the rotor assembly, includes at least one rack gear assembly mechanically coupled on a first end to a portion of the rib cage, wherein the portion of the rib cage moves in response to respiratory-based diaphragm motion.

6. The system of claim 5 further comprising:
    a pinion gear assembly mechanically coupled to the rotor assembly;
    wherein a second end of the at least one rack gear assembly is configured to mesh with the pinion gear assembly;
    wherein linear movement of the rack gear assembly is converted to rotational movement of the pinion gear assembly and the rotor assembly.

7. The system of claim 6 wherein the at least one rack gear assembly includes:
    a magnetic coupling assembly configured to temporarily uncouple the first and second ends of the rack gear assembly during irregular movement of the rib cage.

8. The system of claim 1 wherein the generator assembly includes a coil assembly and a magnetic core assembly axially displaceable within the coil assembly.

9. An implantable system comprising:
    a medical device;
    an energy storage device, electrically coupled to the medical device, for providing electrical energy to the medical device; and
    an implantable generating system electrically coupled to the energy storage device, for converting motion of at least a portion of a rib cage displaceable during respiratory-based diaphragm motion into electrical energy that is provided to the energy storage device, wherein the implantable generating system includes:
        a generator assembly having a rotor assembly and a stator assembly;
        a linkage assembly for mechanically coupling the generator assembly with at least a portion of the rib cage displaceable during respiratory-based diaphragm motion; and
        a freewheel clutch assembly, positioned between the rotor assembly and the linkage assembly, for allowing mono-directional rotation of the rotor assembly independent of the linkage assembly.

10. The system of claim 9 wherein the energy storage device is one of a battery and a capacitor.

11. The system of claim 9 wherein the medical device is chosen from the group consisting of a pacemaker, a defibrillator, a bone growth stimulation device, or a pain attenuation device.

12. The system of claim 9 further comprising a flywheel assembly for storing the rotational kinetic energy of the rotor assembly.

13. The system of claim 9 wherein the linkage assembly, which is configured to convert respiratory-based diaphragm motion into rotational motion of the rotor assembly, includes at least one rack gear assembly mechanically coupled on a first end to a portion of the rib cage, wherein the portion of the rib cage moves in response to respiratory motion.

14. The system of claim 13 further comprising:
    a pinion gear assembly mechanically coupled to the rotor assembly;
    wherein a second end of the at least one rack gear assembly is configured to mesh with the pinion gear assembly;
    wherein linear movement of the rack gear assembly is converted to rotational movement of the pinion gear assembly and the rotor assembly.

15. The system of claim 9 wherein the generator assembly includes:
    a coil assembly and magnetic core assembly axially displaceable within the coil assembly.

* * * * *